US012564585B2

(12) United States Patent
Madhavi et al.

(10) Patent No.: US 12,564,585 B2
(45) Date of Patent: Mar. 3, 2026

(54) NUTRACEUTICALS HAVING SUSTAINED RELEASE FOR IMPROVED BIOAVAILABILITY AND METHOD OF PRODUCTION

(71) Applicant: BioActives LLC, Worcester, MA (US)

(72) Inventors: Doddabele L. Madhavi, Worcester, MA (US); Daniel I. Kagan, Belmont, MA (US)

( * ) Notice: Subject to any disclaimer, the term of this patent is extended or adjusted under 35 U.S.C. 154(b) by 333 days.

(21) Appl. No.: 17/126,811

(22) Filed: Dec. 18, 2020

(65) Prior Publication Data

US 2021/0113554 A1 Apr. 22, 2021

Related U.S. Application Data

(63) Continuation of application No. 14/484,679, filed on Sep. 12, 2014, now Pat. No. 10,898,477, which is a continuation-in-part of application No. 13/943,010, filed on Jul. 16, 2013, now abandoned.

(51) Int. Cl.
| | |
|---|---|
| *A61K 31/4745* | (2006.01) |
| *A23L 33/105* | (2016.01) |
| *A23L 33/12* | (2016.01) |
| *A23L 33/175* | (2016.01) |
| *A61K 9/107* | (2006.01) |
| *A61K 9/16* | (2006.01) |
| *A61K 31/12* | (2006.01) |
| *A61K 31/198* | (2006.01) |
| *A61K 36/00* | (2006.01) |

(52) U.S. Cl.
CPC ........ *A61K 31/4745* (2013.01); *A23L 33/105* (2016.08); *A23L 33/12* (2016.08); *A23L 33/175* (2016.08); *A61K 9/1075* (2013.01); *A61K 9/1617* (2013.01); *A61K 9/1652* (2013.01); *A61K 31/12* (2013.01); *A61K 31/198* (2013.01); *A61K 36/00* (2013.01)

(58) Field of Classification Search
CPC .............. A61K 31/4745; A61K 9/1075; A61K 9/1617; A61K 9/1652; A61K 31/05; A61K 31/12; A61K 31/198; A61K 36/00; A23L 33/12; A23L 33/175; A23L 33/105
See application file for complete search history.

(56) References Cited

U.S. PATENT DOCUMENTS

| | | | | |
|---|---|---|---|---|
| 2003/0229114 A1 * | 12/2003 | Rosenberg | ......... | A61K 31/4745 |
| | | | | 514/291 |
| 2009/0214446 A1 * | 8/2009 | Strassburger | ........... | A23L 27/75 |
| | | | | 424/49 |
| 2011/0305765 A1 * | 12/2011 | Mathur | .................. | A61K 47/36 |
| | | | | 977/773 |

FOREIGN PATENT DOCUMENTS

| | | | | | |
|---|---|---|---|---|---|
| WO | WO-2006062544 A1 * | 6/2006 | ........... | A61K 9/1277 |
| WO | WO-2008134005 A1 * | 11/2008 | ......... | A61K 31/5415 |
| WO | WO-2010070664 A1 * | 6/2010 | ............. | A61K 31/12 |
| WO | WO-2013175507 A1 * | 11/2013 | ........... | A61K 31/047 |

OTHER PUBLICATIONS

Vergallo. Nutraceutical Vegetable Oil Nanoformulations for Prevention and Management of Diseases. Nanomaterials 2020, 10(6), 1232. (Year: 2020).*
Collins English Dictionary, Definition of 'micronized', 2023, 1-3, Key Words for the Pharmaceutical Industry, HarperCollins Publishers.
merriam-webster.com Dictionary, "Micronize.", 2023, 1-7, Merriam-Webster.
Leigh Ann Anderson, What does micronized mean?, Sep. 16, 2022, 1-3, Drugs.com.
Mark Jordi, Ph.D., Laser Light Scattering Particle Sizing Analysis (LLSPSA), Sep. 28, 2017, 1-7, Letter to Bio Actives.

* cited by examiner

*Primary Examiner* — Robert A Wax
*Assistant Examiner* — Olga V. Tcherkasskaya
(74) *Attorney, Agent, or Firm* — Lambert Shortell & Connaughton; David J. Connaughton, Jr.; Justin P. Tinger

(57) ABSTRACT

The present disclosure describes economical processes to improve the bioavailability of nutraceuticals by formulations that induce micronization and sustained release. The inventive process can be used to increase the solubility and bioavailability of lipophilic and moderately water-soluble nutraceuticals by combining excipients that increase the solubility and induce sustained release of the active compounds. The inventive process also can be used to increase the residence time of highly water-soluble nutraceuticals that are metabolized and eliminated quickly from the body, consequently increasing the therapeutic potential. The disclosed formulations advantageously are freely flowing powders that can be used to formulate with other ingredients into tablets, capsules, or the like; or used as bulk powders.

19 Claims, 5 Drawing Sheets

Figure 1. Comparison of dissolution profile of Curcumin and Curcumin-SR powder
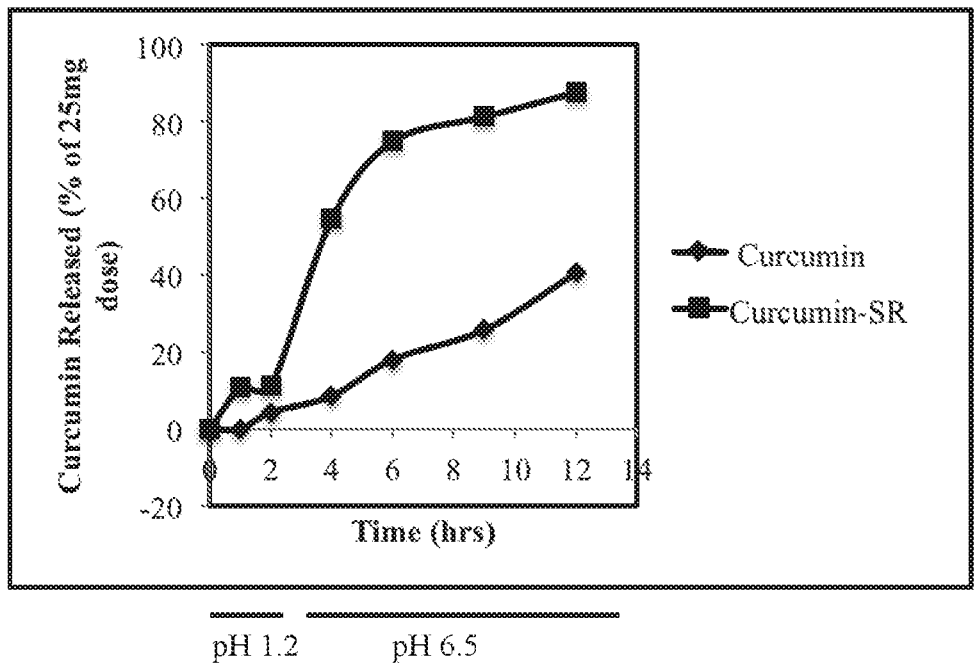
pH 1.2      pH 6.5
Figure 2. Comparison of uptake of Curcumin in a pilot human study
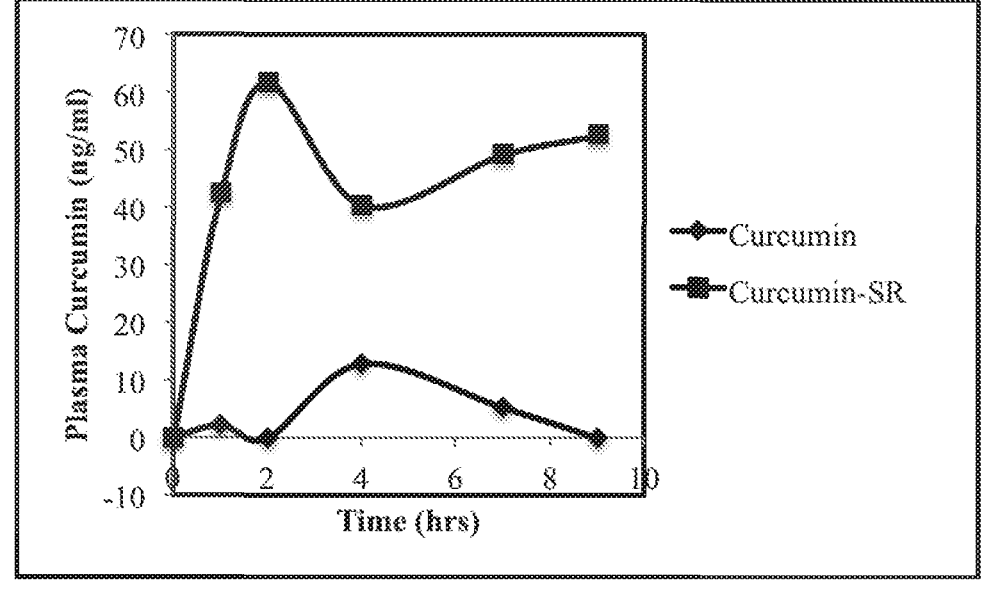

Figure 3. Comparison of dissolution profile of Resveratrol and Resveratrol-SR powder
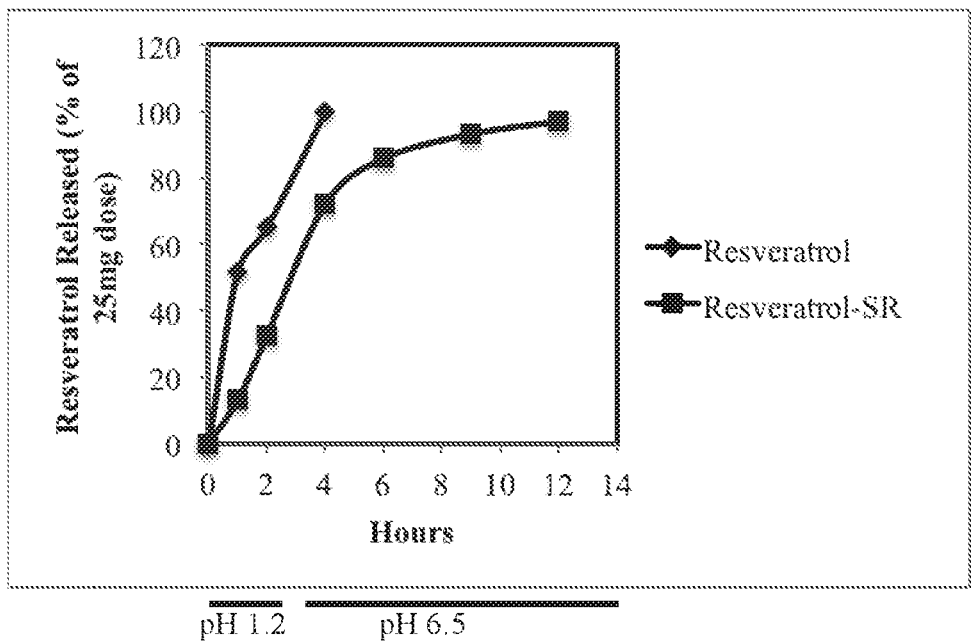
Figure 4. Comparison of total plasma Resveratrol in a pilot human study
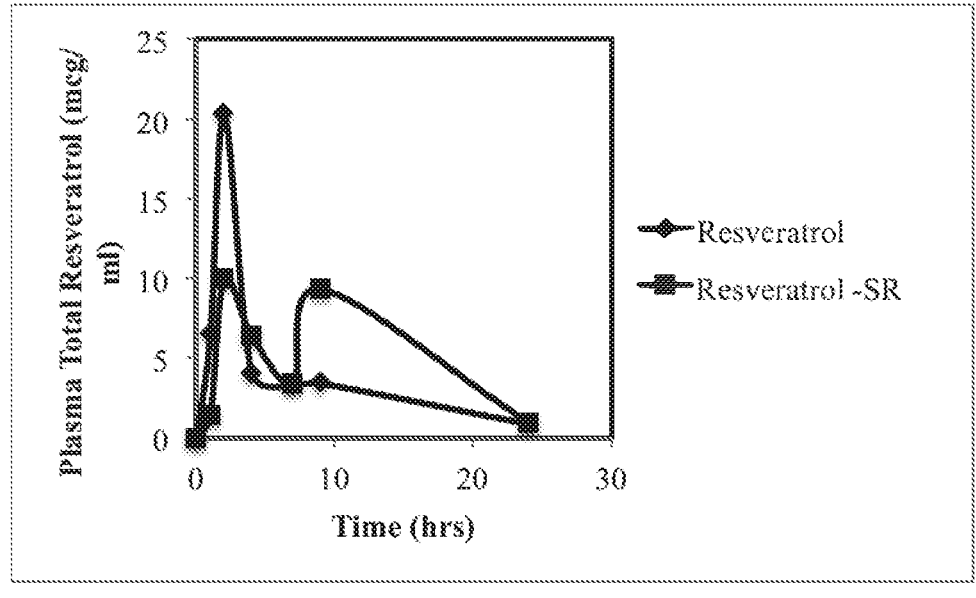

Figure 5. Comparison of free plasma Resveratrol in a pilot human study
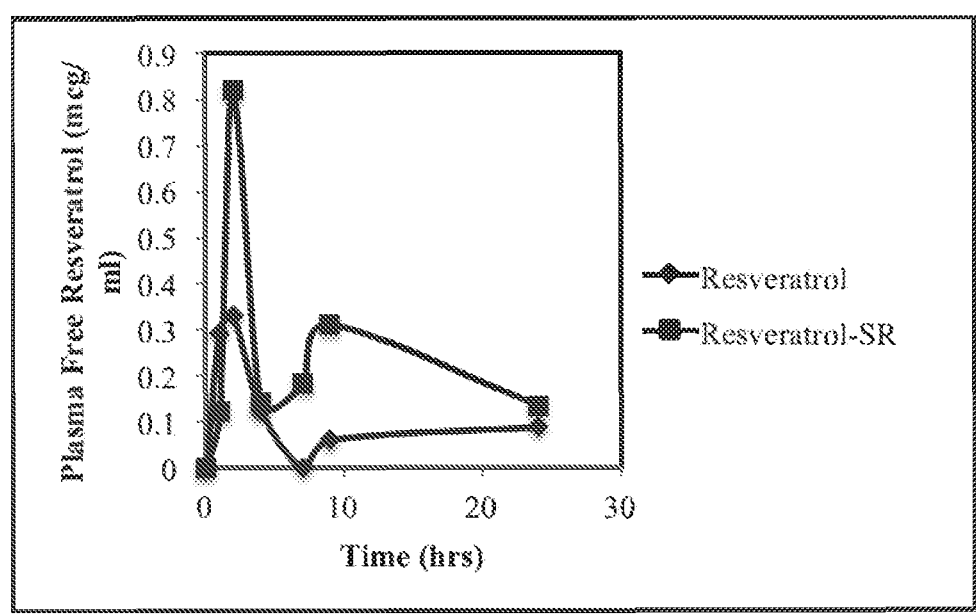
Figure 6. Comparison of dissolution profile of Oligonol and Oligonol-SR powder
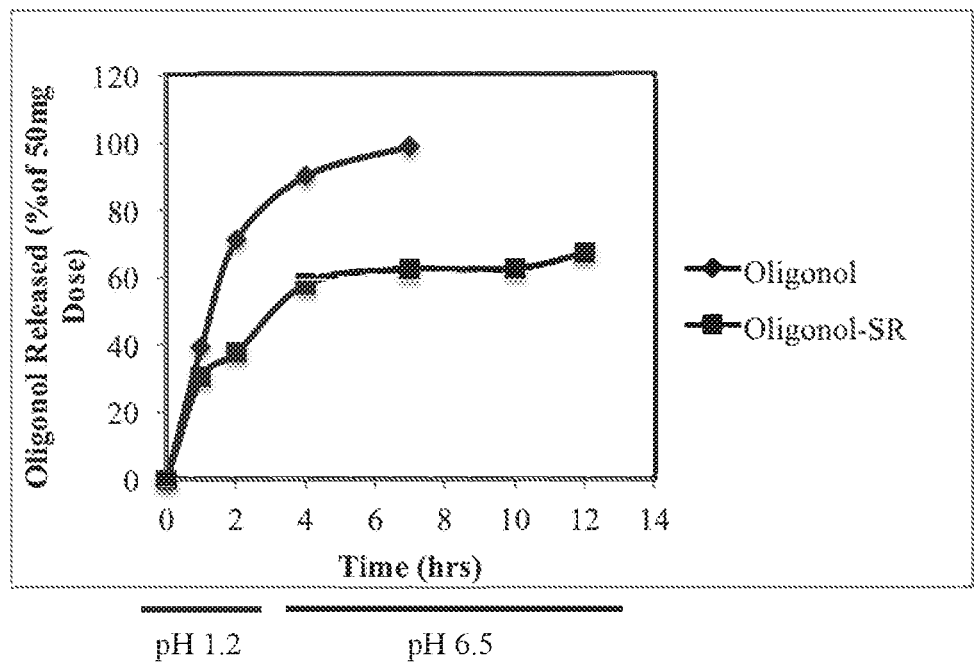

Figure 7. Comparison of uptake of Oligonol in a pilot human study
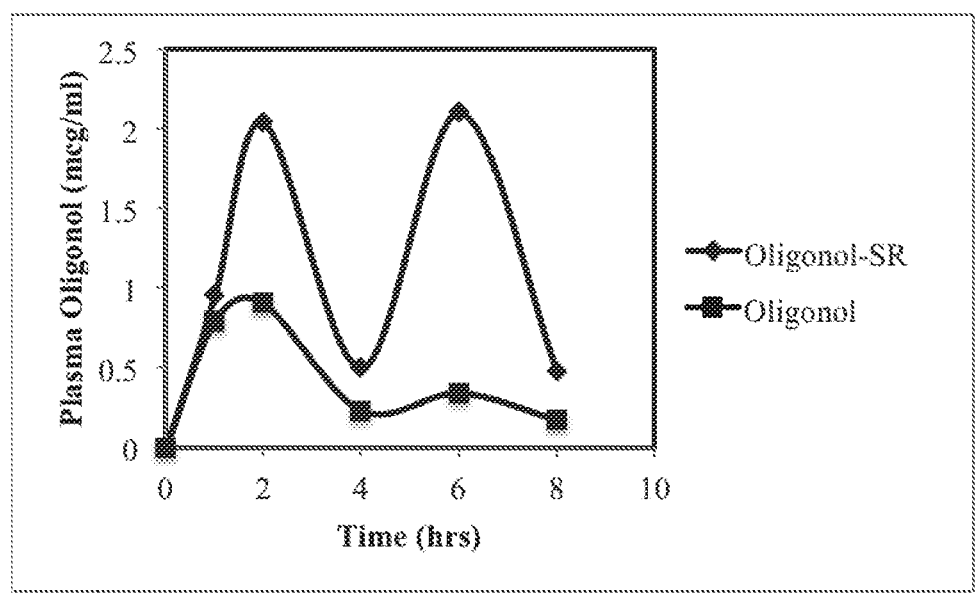
Figure 8. Comparison of dissolution profile of PQQ and PQQ-SR powder
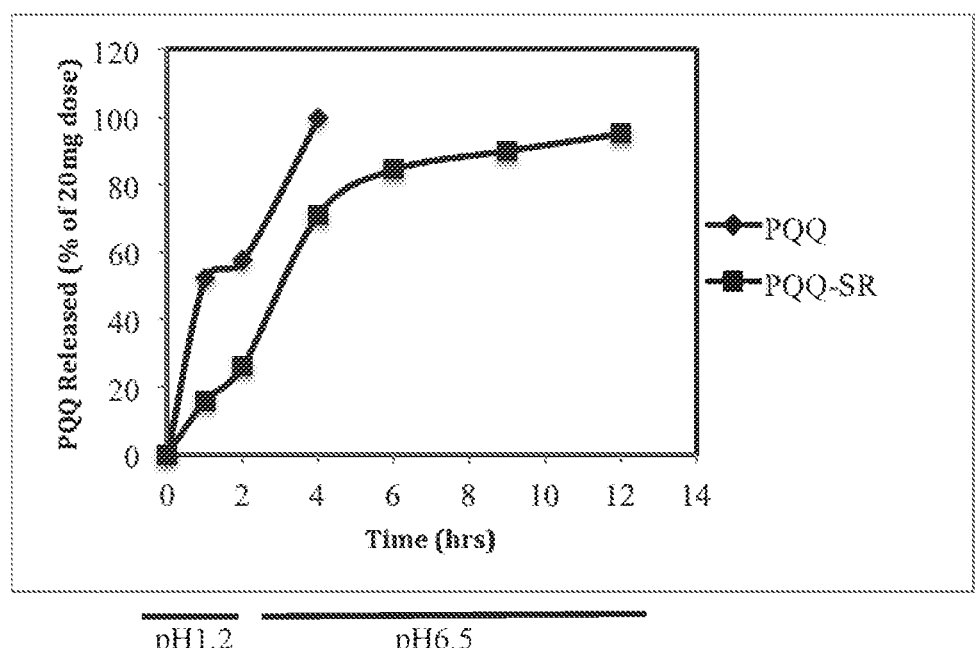

Figure 9. Comparison of uptake of PQQ in a pilot human study
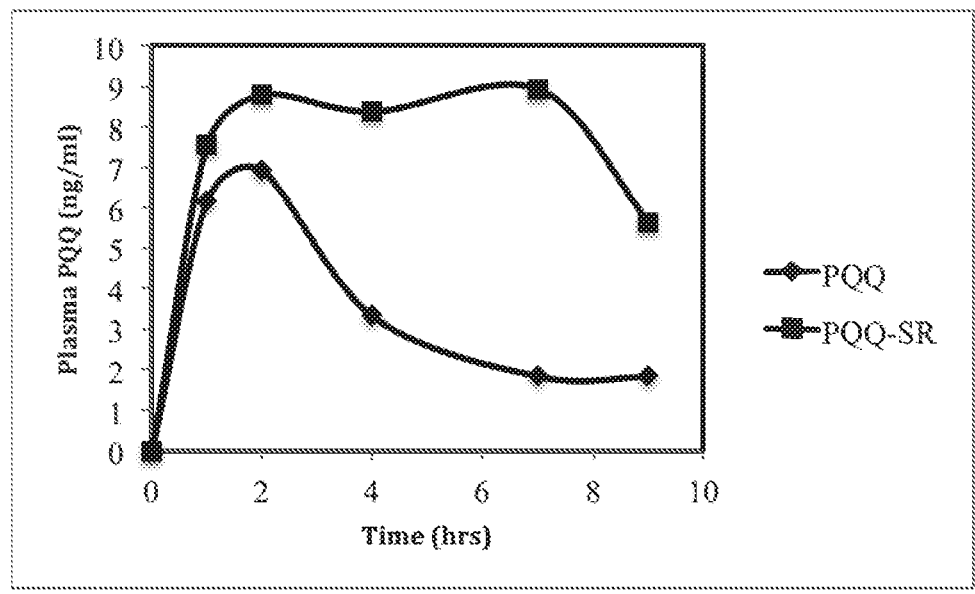

NUTRACEUTICALS HAVING SUSTAINED RELEASE FOR IMPROVED BIOAVAILABILITY AND METHOD OF PRODUCTION

CROSS-REFERENCE TO RELATED APPLICATIONS

This application is a continuation-in-part of application Ser. No. 13/943,010, filed Jul. 16, 2013, the disclosure of which is expressly incorporated herein by reference.

STATEMENT REGARDING FEDERALLY SPONSORED RESEARCH

Not applicable.

BACKGROUND

In recent years, there is an increasing awareness that not all nutraceutical compounds are absorbed upon oral administration. Many lipophilic compounds possess poor oral bioavailability and their absorption is dependent on dietary fats. Also, many highly water-soluble compounds show low therapeutic efficacy, as they are eliminated quickly from the body. One of the main constraints in developing delivery technologies for nutraceuticals is the price sensitive nature of the nutraceutical industry. Many nutraceutical compounds are very inexpensive, while some are very expensive. Any additional processing costs and excipients will increase the cost of the ingredients and make the final dosage form very expensive. Some of the delivery technologies routinely used in the pharmaceutical industry that can be adapted to the nutraceuticals include, for example, microemulsions, self-emulsifying formulations, solid dispersions, and cyclodextrin complexation.

Microemulsions and self-emulsifying formulations generally incorporate a low active compound load of, say, 5%-10%, which is not economical for nutraceuticals. Since the daily dose of nutraceuticals generally are in the range of 50-1000 mg/day, the dosage form either results in big capsules, which are not attractive to consumers, or multiple smaller capsules to meet the required dose per day, which makes the product more expensive. In addition, such formulations are limited to use in soft gelatin capsules and, if converted into a powder, the active compound load is reduced further. They also use high levels of surfactants and co-solvents, such as, for example, ethanol and limonene, which again adds to the cost. Complexing with cyclodextrins also is not economical, as the process involves large amounts of aqueous or organic solvents or kneading equipment. The complex needs to be dried and milled with the active compound load generally around, say, 10%-25%.

Solid dispersions of both hydrophobic and moderately soluble actives in hydrophilic polymers have been reported to improve solubility and bioavailability of nutraceuticals and pharmaceutical compounds. The process uses dissolving the active compound in a solvent and incorporation into the matrix followed by drying or wet granulation of a mixture of the active and polymers followed by drying and milling. The number of steps involved in the process, use of organic solvents, and the equipment necessary makes it uneconomical to use with nutraceuticals.

Another technique, called melt granulation, has been used with some pharmaceuticals. The technique involves using a wax or fat, which is solid at room temperature, as a binder to granulate the active compound with or without additional polymers. The process involves heating the wax with the active or the polymer active mixture under mixing at the melting point of wax. The melted wax forms a coating on the active or the polymer active mixture to form granules. The granules are milled to desired particle size. The prolonged heating involved makes the process not suitable for many nutraceuticals that are heat sensitive.

BRIEF SUMMARY

The present disclosure provides economical methods of improving the bioavailability of nutraceutical compounds. In a first aspect, the disclosure provides a composition for enhancing the solubility and uptake of lipophilic nutraceuticals. The composition comprises a mixture of the active compound with surfactants, oil, and sustained release polymers. The composition is converted into a water dispersible powder that can be formulated with other ingredients.

In a second aspect, the disclosure provides a composition and process for improving the solubility and residence time of moderately water-soluble nutraceuticals. The composition comprises the active compound with sustained release polymers and a lipid component that is a solid at room temperature.

In a third aspect the disclosure provides improved residence time of highly water-soluble nutraceuticals by formulating with a mixture of sustained release polymers and a lipid that is a solid at room temperature.

A first disclosed lipophilic nutraceutical composition, then, includes between about 1% and 60% by weight of a lipophilic nutraceutical composition; between about 0.5% and 20% be weight of a lipid being from one or more of vegetable oils, medium chain triglycerides, and isopropyl or ethyl esters of fatty acids; between about 10% and 30% by weight of a surfactant being one or more of a non-ionic type polysorbate, or polyglycerol esters of fatty acids with a hydrophilic-lipophilic balance (HLB) value between 8-16; between about 1% and 50% by weight of a polymer being one or more of carboxymethyl cellulose, ethyl cellulose, hydroxypropyl methyl cellulose, alginic acid sodium salt, or a cyclodextrin; and between about 1% and 50% by weight of an excipient being one or more of a microcrystalline cellulose, silica, Maltodextrin, potato starch, bamboo silica, or rice flour. This nutraceutical composition has improved sustained release for improved bioavailability.

A method for making the first disclosed lipophilic nutraceutical compositions includes blending a lipophilic nutraceutical composition to a heated, fluent mixture of a lipid and surfactant to form a first blend; blending a polymer with the first blend to form a second blend; cooling the second blend to about room temperature; and blending an excipient with the cooled blend for form a free-flowing powder.

A second hydrophilic nutraceutical compositions includes between about 1% and 60% by weight of a hydrophilic nutraceutical composition; between about 1% and 30% of a lipid that is normally solid at about room temperature; and between about 1% and 50% by weight of a polymer being one or more of carboxymethyl cellulose, ethyl cellulose, hydroxypropyl methyl cellulose, alginic acid sodium salt, a dextrin, carrageenan, or a cyclodextrin; provided that between about 1% and 30% by weight of a cyclodextrin is included. This nutraceutical composition has sustained release for improved bioavailability.

A method for making the second hydrophilic nutraceutical composition includes milling a hydrophilic nutraceutical composition with a polymer and a cyclodextrin; heating the milled product; forming a heated, fluent lipid; and spraying said heated, fluent lipid onto said heated milled product to for free-flowing granular powder.

These and other products and methods will be apparent to those skilled in this art field based on the present disclosure.

BRIEF DESCRIPTION OF THE DRAWINGS

For a fuller understanding of the nature and advantages of the present method and process, reference should be had to the following detailed description taken in connection with the accompanying drawings, in which:

FIG. 1 shows the comparison of dissolution profile of Curcumin and Curcumin-SR powder;

FIG. 2 shows the comparison of uptake of Curcumin in a pilot human study;

FIG. 3 shows the comparison of dissolution profile of Resveratrol and Resveratrol-SR powder;

FIG. 4 shows the comparison of total plasma Resveratrol in a pilot human study;

FIG. 5 shows the comparison of free plasma Resveratrol in a pilot human study;

FIG. 6 shows the comparison of dissolution profile of Oligonol and Oligonol-SR powder;

FIG. 7 shows the comparison of uptake of Oligonol in a pilot human study;

FIG. 8 shows the comparison of dissolution profile of PQQ and PQQ-SR powder; and FIG. 9 shows the comparison of uptake of PQQ in a pilot human study.

The drawings will be described in greater detail below.

DETAILED DESCRIPTION

Disclosed are economical processes where induced micronization and sustained release result in improved bioavailability. The inventive processes can be used to increase the solubility and bioavailability of lipophilic nutraceuticals and moderately water-soluble nutraceuticals by combining excipients that increase the solubility and induce sustained release of the active compounds. The inventive processes also can be used to increase the residence time of highly water-soluble nutraceuticals that are metabolized and eliminated quickly from the body, consequently increasing their therapeutic potential. The disclosed formulations advantageously are powders that can be used with other ingredients in the form of tablets or capsules or as bulk powders. The nutraceutical is present in an amount of between about 1% and 60% by weight of the composition and can range from between about 2% to 50% by weight of the composition. The nutraceutical is in a micronized form with particle size not substantially greater than about 10μ and forms a fine dispersion in water.

It was surprisingly found that incorporating optimal amounts of polymers induces sustained release in the formulations and increases the bioavailability of both lipophilic and hydrophilic compounds. Heretofore, sustained release formulations have been widely used in pharmaceuticals to provide constant or nearly constant drug levels in the plasma. While such formulations generally result in longer $T_{max}$ (time to reach maximum plasma concentration) and lower $C_{max}$ (peak plasma concentration), the bioavailability, as determined by area under the curve (AUC), in general does not differ from the immediate release forms of the drug, unlike the inventive formulations disclosed.

It also was surprisingly found that the $T_{max}$ was not altered in the inventive formulations and the $C_{max}$ was higher especially with the highly water soluble compounds compared to the unformulated nutraceutical. This indicates that the inventive formulations have both immediate release and sustained release properties. Also, such formulations typically are sold as solid dosage forms, while the powders made in accordance with the present disclosure can be used as ingredients in formulations.

The optimal amount of polymers is an amount insufficient to coat all of the particles formed. Thus, both immediate release (uncoated particles) and sustained release (coated particles) are achieved. Immediate release permits the body to absorb that amount immediately released without overwhelming the body's ability to handle more, while the sustained release then permits the body to continue to use the nutraceutical over time.

Suitable lipophilic nutraceuticals that can be formulated with the present disclosure include, for example, but are not limited to, mixed carotenoids, carotenoid esters, Curcuminoids, Policosanol, Silymarin, Baicalein, Quercetin, plant sterols, vitamins (such as, for example, Vitamin E and A), alpha lipoic acid, sesquiterpene lactones (such as, for example, parthenolides), and mixtures thereof. Curcumin was chosen as an example of the lipophilic compounds to illustrate the present disclosure; but its use is by way of example and not limitation.

Curcumin is isolated from turmeric root, which is widely used as a spice and food color in India. Purified Curcumin contains at least 77% Curcumin, 17% demethoxycurcumin, and 6% bisdemethoxycurcumin. Curcumin has shown several beneficial effects, such as, for example, potent antioxidant, anti-inflammatory, anti-cancer, wound healing, and hepatoprotective activities in cell based and animal studies (Anti-inflammatory properties of Curcumin, a major constituent of *Curcuma longa:* A review of preclinical and clinical research, Jurenka, J. S., Alt. Med. Rev., 14: 141-153, 2009). However, Curcumin also is water insoluble and has poor oral bioavailability in human and animal studies. Because of the poor oral bioavailability, very high oral doses and repeated dosing are being tried to obtain effective plasma levels. Curcumin has a strong spicy taste and at high dose levels causes gastric disturbance, which often results in poor patient compliance.

Several formulating methods have been reported to improve the solubility and bioavailability of Curcumin, including, for example, using combinations of surfactants, co-surfactants, oils, and/or organic solvents to form microemulsion or self emulsifying systems, and solid dispersions in water soluble carriers. The microemulsion and self-emulsifying formulations also have been converted into powders by using excipients such as, for example, microcrystalline cellulose, starch, and Maltodextrin. These formulations have many disadvantages. Curcumin is fully solubilized in these formulations and the amount dissolved is limited by the solubility of Curcumin in the surfactant-oil mixtures. Hence, Curcumin concentration generally is less than 10%-15% in such systems. On further conversion into a powder, the concentration is further reduced with the result that the solid dosage forms, such as tablets or capsules, have to be larger or a greater number of tablets or capsules are needed to meet therapeutic dose, which reduces patient compliance. Also, if the microemulsion or self-emulsifying formulations are not converted into powders, the liquid formulations are limited to incorporation into soft gelatin capsules, which makes the final product more expensive (Novel self-emulsifying formulation of Curcumin with improved dissolution, antiangiogenic and anti-inflammatory activity, Ramshankar, Y. V., Suresh, S., and Devi, K., Olin. Res. Regulatory Affairs, 25: 213-234, 2008; Preparation and enhancement of oral bioavailability of Curcumin using microemulsions vehicle, A. Agric. Food Chem., 60: 7137-7141. 2012); Method of enhancing dissolution properties of relatively insoluble dietary supplements and product incorporating the same, Goldman, R., U.S. Pat. No. 6,056,971). Solid dispersions of Curcumin in water-soluble carriers also have been developed. Such methods generally involve colloidal milling to reduce the particle size, a drying step, such a spray drying or freeze drying if the composition is converted into a powder, which again makes the final dosage form more expensive (Innovative preparation of Curcumin for improved oral bioavailability, Sasaki, H., Sunagawa, Y., Takahashi, K., Imaizumi, A., Fukuda, H., Hashimoto, T., Wada, H., Katanasaka, Y., Kakeya, H., Fujita, M., Hasegawa. K., and Morimoto, T., Biol. Pharm. Bull, 34; 660-665, 2011; Dissolution and absorption researches of Curcumin in solid dispersions with the polymers PVP, Xu, D., Wang, S., Jin, J., Mei, X., Xu, S., Asian J. Pharmacodynamics Pharmacokinetics, 6:343-349, 2006; polymeric nanoparticle-encapsulated Curcumin (Nanocurcumin): A novel strategy for human cancer therapy, Bisht, S., Feldmann, G., Soni, S., Ravi, R., Karikar, C., Maitra, A., Maitra, A., J. Nanobiotech., 5: 1-18, 2007). The disclosed nutraceutical particles are formed using simple mixing equipment, such as, for example, a jacketed kettle with overhead mixer and ribbon blender, which makes the equipment investment less expensive and production less expensive.

One of the disclosed compositions includes oil, surfactant, polymers, and excipients that are generally recognized as safe (GRAS) and widely used in the food, pharmaceutical, and dietary supplements. The oil preferably is selected from vegetable oils, medium chain triglycerides, and isopropyl or ethyl esters of fatty acids. The surfactant preferably is selected from non-ionic type polysorbate materials and polyglycerol esters of fatty acids with a hydrophilic-lipophilic balance (HLB) value between about 8 and 16. The polymers can be selected from carboxymethyl cellulose, ethyl cellulose, hydroxypropyl methyl cellulose (HPMC, varying viscosity), alginic acid sodium salt (varying viscosity), and cyclodextrins (natural and modified). The excipients can be selected from microcrystalline cellulose, silica (e.g., Syloid® silica, registered trademark of W. R. Grace & Co. Corporation, New York, NY), maltodextrin, potato starch, bamboo silica, and rice flour.

The oil can be used in an amount of between about 0.5% and 20% by weight of the composition and can be used between about 1% and 7% by weight of the composition. The surfactant can be used in an amount of between about 1% and 40% by weight of the composition, and can range between about 10% and 30% by weight of the composition. The polymers can be used singly or in combination in an amount of between about 1% and 50% by weight of the composition, and can be between about 10% and 20% by weight of the composition. The excipients to convert the composition into a powder can be used singly or in combination in an amount of between about 1% and 50% by weight of the composition, and can be between about 10% and 40% by weight of the composition.

The inventive process for formulating hydrophobic compounds is described herein. In brief, Curcumin was slowly added to a mixture of Polysorbate 80 and isopropyl myristate heated to 70° C. under stirring in a jacketed kettle. Initially, Curcumin started to dissolve followed by the formation of a supersaturated solution and a fine dispersion. The polymers HPMC (hydroxypropyl methylcellulose) and sodium alginate were mixed into the hot dispersion and the resulting paste was allowed to cool to room temperature.

The paste was converted into a free flowing powder by adding silica using a ribbon blender. The Curcumin-sustained release (SR) powder was water dispersible and contained 25% Curcumin. It also was surprisingly found that the Curcumin-SR powder was tasteless with no spicy notes when dispersed in water. The powder can be used dispersed in foods such as, for example, smoothies and yogurt.

In the dissolution test, the Curcumin-SR powder showed a significantly higher dissolution and sustained release of Curcumin as compared to pure Curcumin powder both in the simulated gastric and intestinal fluids. It was surprisingly found that Curcumin was in a micronized form in the composition.

In a pilot human uptake study, the Curcurmin-SR powder showed superior absorption and sustained release compared to Pure Curcumin powder. The average area under the curve $(AUC_{0-9hr\ ng/(ml*hr)})$ for Curcumin-SR was 412.14 and for the control curcumin 47.78. The ratio of Curcumin-SR to Curcumin powder AUC was 8.6. In a pilot human tolerance study, high doses of Curcumin-SR powder at 1-3 tablespoonfuls (3-11 g Curcumin) per day for 90 days did not cause any adverse events such as gastrointestinal upset and nausea.

Examples of moderately soluble and highly soluble nutraceuticals that can be formulated with the present disclosure include, but are not limited to, phenolic compounds (such as, for example, Resveratrol), rutin, polyphenols (such as, for example, a mixture of low molecular weight polyphenols derived from high molecular weight proanthocyanidins from lychee fruit and green tea, sold under the trademark Oligonol®), catechins, bioactive polysaccharides (such as, for example, Active Hexose Correlated Compound or AHCC, an alpha-glucan rich nutritional supplement produced from the mycelia of shiitake), cofactors (such as, for example, pyrroloquinoline quinone (PQQ)), and amino acids (such as, for example, arginine and glutamine). Resveratrol was chosen as an example of moderately water-soluble compounds to illustrate the present disclosure. Oligonol and PQQ were chosen as examples of the highly water soluble compounds to illustrate the present disclosure.

Resveratrol (3,4',5-trihydroxy-trans-stilbene) is a polyphenol of the stilbene family. The major dietary sources of Resveratrol include grapes, red wine, and peanuts. Resveratrol has shown anti-inflammatory, antioxidant, and anti-aging properties in cell based and animal studies. It has been shown to lower incidence of coronary artery disease and to possess cancer chemopreventive properties (Resveratrol monograph, *Alt Med Rev.*, 15: 15-158, 2010). Orally administered Resveratrol is absorbed rapidly, metabolized extensively, and eliminated, resulting in trace amounts of unchanged Resveratrol in systemic circulation. It is of interest to improve the solubility and residence time to enhance the therapeutic effects of Resveratrol. Some of the strategies used in the industry include, for example, formulating Resveratrol with compounds that inhibit the conjugation of Resveratrol (marketed by Longevinex®, Resveratrol Partners, LLC, North Las Vegas, NV), form a dispersion of Resveratrol in oil whose components function synergistically with Resveratrol (U.S. Patent Publication 2013/0040920A-1), and formulating Resveratrol with a sustained release polymer into a final dosage form (marketed by Biotivia®, James Betz, Marina del Rey, CA).

Oligonol® (Amino Up Chemical Co., Japan) is a mixture of low molecular weight polyphenols derived from high molecular weight proanthocyanidins from lychee fruit and green tea. Several clinical studies have shown that Oligonol® product has beneficial properties, such as, for example, anti-inflammatory and antioxidant activity, microcirculation improvement, and visceral fat reduction in obese subjects (Amelioration of abdominal obesity by low molecular weight polyphenol (Oligonol) from Lychee, Nishihara, J., Sato-Ueshima, M., Kitadate, K., Wakame, K., Fujii, H., J. Functional Foods, 1: 341-348, 2009; Antioxidative effects of a new Lychee fruit-derived polyphenol mixture, Oligonol, converted into a low molecular weight form in adipocytes, Sakurai, T., Nishioka, H., Fujii, H., Nakano, N., Kizaki, T., Radak, Z., Izawa, T., Haga, S., and Ohno, H., Biosci. Biotechnol. Biochem., 72: 463-476, 2008; Effect of Oligonol on increasing peripheral body temperature, Report, Amino Up Chemical Co., Ltd., Japan). Oligonol® product is water soluble with limited bioavailability. In human studies, the maximum plasma level was reached 2 hrs after ingestion and the levels reached baseline by 8 hours. Oligonol® product is an expensive product with a cost of about $1,500/kg and the effective dose is 200 mg/day. Thus, increasing the uptake of Oligonol® product to decrease the amount of effective dosage per day is of interest to both manufacturers of final dosage forms and consumers.

PQQ (Pyrroloquinoline quinone) is a ubiquitous cofactor for several enzymes and catalyzes repeated reduction oxidation reactions as well as oxidative deaminations. It is involved in cell signaling pathways, and is reported to play a role in mitochondriogenesis in animal studies. PQQ supplementation is reported to have several beneficial effects on cognitive, immune, cardiac and antioxidant functions (Potential physiological importance of Pyrroloquinoline, Rucker R., Chowanadisai, W., and Nakano, M., *Alt, Med, Rev.,* 14: 268-277, 2009). PQQ is a highly water-soluble molecule, which is absorbed and eliminated quickly from the system. In human studies, the maximum plasma level was reached 2 hrs after ingestion and the levels reached baseline by 8 hrs. PQQ is an expensive product with a cost of $9,000/kg and the effective dose is 10-20 mg/day. Thus, increasing the uptake of PQQ and the residence time for improved therapeutic benefits is of interest to both manufacturers of final dosage forms and the consumers.

The disclosed inventive compositions for Resveratrol, PQQ and Oligonol formulations contain polymers, cyclodextrin, and a lipid component that are generally recognized as safe (GRAS) and widely used in the food, pharmaceutical, and dietary supplements. The polymers can be selected from carboxymethyl cellulose, ethyl cellulose, hydroxypropyl methylcellulose (HPMC, varying viscosity), alginic acid sodium salt (varying viscosity), dextrins, carrageenan and cyclodextrins (natural $\alpha$-, $\beta$-, and $\gamma$-cyclodextrins and modified cyclodextrins). The lipid component is selected from fats that are solid at room temperature, which includes saturated fats (such as, for example, coconut oil, hydrogenated fats, glycerol esters of fatty acids), and food grade waxes (such as, for example, carnauba wax, beeswax, paraffin wax), shellac and the like.

The polymers are used singly or in combination in an amount of between about 1% and 50% by weight of the composition, and can be between about 10% and 20% by weight of the composition. The cyclodextrins are used singly or in combination in amounts of between 1% and 30% by weight of the composition, and can be between 5% and 15% by weight of the composition. The lipid components are used singly or in combination in amounts of between about 1% and 30% by weight of the composition, and can be between 5% and 20% by weight of the composition. As stated above, the amount of polymers and lipid components used is insufficient to coat all of the particles being formed, resulting in immediate release and sustained release particles. The coated particles are less than about 10μ in size.

The inventive process for formulating moderately water-soluble and highly water-soluble compounds is described herein. In brief, the compound was co-mixed with the cyclodextrins and polymers. The blend was transferred to a jacketed ribbon blender and warmed to between 30°-35° C. The lipid component was melted at the melting point of the lipid and sprayed onto the blend under mixing. The resulting mixture of the blend and agglomerates can be milled or sieved to pass through a 40-mesh sieve to form a free-flowing granular powder.

In the dissolution test, the formulated powders showed sustained release of the active molecule as compared to the unformulated active molecule over a period of 12 hrs in the USP (United States Pharmacopeia) dissolution test for extended release compounds consisting of simulated gastric and intestinal fluids. It also was surprisingly found that the active molecule was in a micronized form in the formulations.

The uptake of formulations was tested in pilot human studies. In a pilot human uptake study, Resveratrol powder showed a rapid absorption with a sharp peak at $T_{max}$ of 2 hrs post-dose. After 2 hrs, the plasma levels of total Resveratrol declined rapidly with a small increase at 9 hrs. Resveratrol-SR also showed a $T_{max}$ at 2 hrs, but a lower $C_{max}$ with a broader peak and higher plasma levels compared to the control for >9 hrs. The ratio of Resveratrol-SR to control Resveratrol AUC was 2.54.

In a pilot human uptake study, Oligonol-SR formulation showed a higher plasma Oligonol level at $T_{max}$ (2 hrs) compared to Oligonol powder followed by a second prominent absorption peak at 6 hrs post dose and a higher plasma level at 8 hrs post dose. The ratio of Oligonol-SR to Oligonol powder AUC was 2.39.

In a pilot human uptake study pyrroloquinoline quinone-sustained release (PQQ-SR) showed a higher plasma PQQ level at $T_{max}$ of 2 hr compared to PQQ powder followed by sustained release till 9 hrs. The plasma levels remained high at 9 hrs, indicating sustained release for >9 hrs. The control PQQ powder showed a $T_{max}$ at 2 hrs and the plasma level reached near baseline by 9 hours. The ratio of PQQ-SR to control PQQ AUC was 2.2.

The following examples show how the present disclosure has been practiced, but should not be construed as limiting.

EXAMPLES

Example 1. Curcumin-SR Formula

Curcumin (95%) was slowly dispersed in a heated mixture of polysorbate 80 and isopropyl myristate at 70° C. in a jacketed kettle with stirring. Initially Curcumin started to dissolve in the surfactant oil mixture to form a reddish solution. Further addition of Curcumin resulted in the formation of a yellow dispersion. The dispersion was stirred for 15-20 min. HPMC and sodium alginate polymers were added while the mixture was held at 70° C. and mixed into the free flowing paste. The resulting thick paste was allowed to come to room temperature. The paste was converted into a free flowing powder using Syloid silica in a ribbon blender. The final formulation Curcumin-SR is a yellow water dispersible powder containing 25% Curcumin suitable for hard gelatin capsules, tablets and as bulk powder to be incorporated into shakes, juices or as a water dispersion.

Curcumin-SR Dissolution Test

The objectives of the study were to determine the in vitro dissolution profile of Curcumin-SR formulation in comparison with 95% pure Curcumin powder. The studies were done using a bio-relevant media, which can predict the bioavailability in vivo.

Samples Tested

Curcumin powder (95% Curcumin).
Curcumin-SR powder (25% Curcumin).

Dissolution Test

The in vitro dissolution study was performed using the Varian 7020 dissolution tester with the basket configuration at 37° C., 100 rpm. The samples equivalent to 25 mg Curcumin filled in hard gelatin capsules were used for the study. The capsules were introduced into 750 ml of 0.1N HCl (simulated gastric fluid without enzymes, SGF) maintained at 37° C. At the end of 1 and 2 hrs, 3 ml of the sample was withdrawn and filtered through 10µ-syringe filter. The removed volume was replaced each time with fresh medium. At the end of 2 hr, the pH of the medium was adjusted to 6.5 (simulated intestinal fluid without enzymes, SIF) with 195 ml of 0.2M tribasic sodium phosphate solution equilibrated to 37° C. Polysorbate 80 dissolved in 55 ml of water was added to a concentration of 0.25% to simulate intestinal fluid. Aliquots were withdrawn at 4, 6, 9, and 12 hrs for analysis, as described before, and the removed volume was replaced with fresh medium each time. The aliquots were diluted with methanol for the HPLC analysis of Curcumin. Curcumin was quantified using reverse-phase HPLC on a Phenomenex Luna column (150×4.6 mm, 5 µm) at room temperature. The samples were eluted using an isocratic mobile phase consisting of 5% acetic acid/45% and acetronitrile/55%. The flow rate was 1 ml/min and detection wavelength was 420 nm. Standard Curcumin from Chromadex was used for quantification. The retention time for Curcumin was 5.2 min under these conditions.

Observations

Curcumin has little or no solubility in the gastric fluid and low solubility in the intestinal fluid. It exists as a neutral molecule between pH 1-7, so the typical pH range in the stomach or intestine has very little effect on the solubility. When released in vivo or in vitro from solubilized formulations, Curcumin can rapidly precipitate out as the saturation point is reached. The polymers in the present formulation function as precipitation inhibitors and can maintain the supersaturated state for prolonged periods of time. The polymers also stabilize the formulation and control the release of the micronized curcumin.

The dissolution profile (FIG. 1) shows a sustained release of Curcumin from the Curcumin-SR formula. Nearly 10% of the dose was released at acidic pH by 2 hours. By 12 hrs, ~88% of the dose was in solution in a micronized form, less than 10 microns particle size. The initial dissolution helps in incorporation of Curcumin into the gastric digesta. In the intestines, the sustained release in the presence of the bile acids results in incorporation into mixed micelles facilitating overall uptake of Curcumin. With the 95% pure Curcumin, very little is micronized or released at the gastric pH, which limits the incorporation or dissolution in the gastric digesta. Consequently, when the 95% pure Curcumin enters the intestines, it will be in an insoluble form, which again limits the incorporation into mixed micelles and uptake.

Curcumin-SR Bioavailability: A Pilot Study

The objective of this human study was to determine the uptake of Curcumin-SR powder in comparison with 95% pure Curcumin powder.

Clinical Study Protocol

Curcumin-SR formulation and Curcumin powder equivalent to 250 mg total Curcuminoids were used for the study. The samples were provided in hard gelatin capsules. The crossover study was done using two healthy subjects who were not using curcumin in their food preparations or consuming Curcumin supplements. On the day of the study, 7 ml of blood was collected in EDTA tubes to permit establishment of baseline value. Curcumin-SR capsules were administered after breakfast and blood samples were drawn as before at 1, 2, 4, 7, and 9 hrs post-dose. The samples were stored on ice protected from light and the plasma was separated by centrifugation within 1 hr of collection and stored at −70° C. until analysis. After a 7-day washout period the protocol was repeated for the control Curcumin powder capsules.

Curcumin Extraction and Analysis

Hydrolysis of Curcumin conjugates and extraction of Curcumin from the plasma were done based on the method described by Vareed et at. (Pharamcokinetics of curcumin conjugate metabolites in healthy human subjects, *Cancer Epidemiol Biomarkers,* 17: 1411-1417, 2008). One ml of the plasma was incubated with 2000 units of β-glucuronidase and 260 units sulfatase at 37° C. for 3.5 hrs. The samples were extracted three times with ethyl acetate/methanol (95:5) and the solvents were evaporated under nitrogen protected from light. The residue was dissolved in methanol (0.2 ml) for HPLC analysis. Curcumin was quantified using reverse-phase HPLC as described above.

Results and Observations

FIG. 2 presents the uptake of Curcumin from Curcumin-SR and 95% curcumin powder. Curcumin-SR showed a $T_{max}$ of 2 hr followed by sustained release until 9 hrs. The plasma levels remained high at 9 hrs, indicating sustained release for >9 hrs. The Curcumin powder showed a $T_{max}$ at 4 hrs and the plasma level reached baseline by 9 hours. The average area under the curve ($AUC_{0-9hr\ ng/(ml*hr)}$) for Curcumin-SR was 412.14 and for the control curcumin 47.78. The ratio of Curcumin-SR to Curcumin powder AUC was 8.6. The results indicate the superior bioavailability of Curcumin-SR with a reduction in time to reach maximum blood levels ($T_{max}$) and sustained release for >9 hrs.

Example 2. Resveratrol-SR Formula

Resveratrol (98%) was formulated using a combination of HPMC, β-cyclodextrin, and Carnauba wax. The final product Resveratrol-SR is an off-white granular water dispersible powder containing 30% Resveratrol, suitable for hard gelatin capsules and tablets.

Resveratrol-SR Dissolution Test

The objectives of the study were to determine the in vitro dissolution profile of Resveratrol-SR formulation in comparison with 98% pure Resveratrol powder. The studies were done using a bio-relevant media, which can predict the bioavailability in vivo.

Samples Tested

Resveratrol powder (98%)
Resveratrol-SR powder (30%)

Dissolution Test

The in vitro dissolution study was performed using the Varian 7020 dissolution tester with the basket configuration at 37° C., 100 rpm. The samples equivalent to 25 mg Resveratrol filled in hard gelatin capsules were used for the study. The capsules were introduced into 750 ml of 0.1N HCl (simulated gastric fluid without enzymes, SGF) maintained at 37° C. At the end of 1 and 2 hrs, 3 ml of the sample was withdrawn and filtered through 10µ-syringe filter. The removed volume was replaced each time with fresh medium. At the end of 2 hr, the pH of the medium was adjusted to 6.5 (Simulated intestinal fluid without enzymes, SIF) with 195 ml of 0.2M tribasic sodium phosphate solution equilibrated to 37°C. Polysorbate 80 dissolved in 55 ml of water was added to a concentration of 0.25% to simulate intestinal fluid. Aliquots were withdrawn at 4, 6, 9, and 12 hrs for analysis as described before and the removed volume was replaced with fresh medium each time. The aliquots were diluted with methanol for HPLC analysis. Resveratrol was quantified using reverse-phase HPLC on a Phenomenex Prodigy column (250×4.6 mm, 5 µm) at room temperature. The samples were eluted using an isocratic mobile phase consisting of 5% acetic acid/55% and methaniol/45%. The flow rate was 1 ml/min and detection wavelength was 306 nm. The retention time for Resveratrol was 7.5 min under these conditions. Standard Resveratrol from Sigma was used for calibration.

Observations

Since Resveratrol has low solubility in water, the dissolution study was done under sink conditions to allow enough media for complete dissolution. FIG. 3 presents the dissolution profile of Resveratrol powder and Resveratrol-SR. The Resveratrol powder showed complete dissolution (100%) in 4 hours. The Resveratrol-SR formula showed sustained release over a period of 12 hrs, with 97% of the dose released at 12 hrs.

Resveratrol-SR Bioavailability: A Pilot Study

The objective of this human study was to determine the uptake of Resveratrol-SR powder in comparison with 98% Resveratrol powder.

Clinical Study Protocol

Resveratrol-SR formulation and 98% Resveratrol powder equivalent to 500 mg Resveratrol were used for the study. The samples were provided in hard gelatin capsules. The crossover study was done using two healthy subjects who were not consuming Resveratrol supplements. The subjects were asked not to consume Resveratrol containing foods, such as, peanuts grapes and wine, for 48 hours before the study. On the day of the study, 7 ml of blood was collected in EDTA tubes to permit establishment of baseline value. Resveratrol-SR capsules were administered after breakfast and blood samples were drawn as before at 1, 2, 4, 7, 9, and 24 his post-dose. The samples were stored on ice protected from light and the plasma was separated by centrifugation within 1 hr of collection and stored at −70° C. until analysis. After a 7-day washout period the protocol was repeated for the control Resveratrol powder capsules.

Resveratrol Extraction and Analysis

Plasma total Resveratrol (Resveratrol conjugates and free Resveratrol) and free Resveratrol were determined based on the method described by Meng et al. (Urinary and plasma levels of resveratrol and quercetin in humans, mice and rats after ingestion of pure compounds and grape juice, *J. Agric. Food Chem.*, 52: 935-942, 2004).

For total Resveratrol analysis, 0.5 ml of the plasma was incubated with 1000 units of β-glucuronidase and 130 units sulfatase at 37° C. for 1 hr. Adding 0.5 ml methanol to the plasma samples precipitated the proteins. The mixture was extracted twice with 2.5 ml ethyl acetate and the solvent was evaporated under nitrogen protected from light. The residue was dissolved in the mobile phase 5% acetic acid/55% and methanol/45% (0.2 ml) for HPLC analysis. For free Resveratrol analysis, the samples were extracted as described without enzyme hydrolysis. Resveratrol was quantified using reverse-phase HPLC as described above.

Results

FIG. 4 presents the plasma total Resveratrol profile from Resveratrol-SR and 98% Resveratrol powder. Resveratrol powder showed a rapid absorption with a sharp peak at $T_{max}$ of 2 hrs post-dose. After 2 hrs, the plasma levels of total Resveratrol declined rapidly with a small increase at 9 hrs. Resveratrol-SR also showed a $T_{max}$ at 2 hr, but a lower $C_{max}$ (maximum concentration at $T_{max}$) with a broader peak and higher plasma levels compared to the control for >9 hrs.

The free Resveratrol profile (FIG. 5) indicates higher plasma levels with Resveratrol-SR, which was maintained for >9 hrs compared to the control. The average area under the curve ($AUC_{0-24hr\ mcg/(ml*hr)}$) for free Resveratrol was 5.84 (Resveratrol-SR) and 2.29 (Resveratrol powder). The ratio of Resveratrol-SR to Resveratrol powder AUC was 2.54.

Observations

Pure Resveratrol powder is absorbed rapidly, metabolized extensively, and eliminated, resulting in trace amounts of unchanged Resveratrol in systemic circulation. The results of the study indicate that Resveratrol-SR formulation extends the systemic exposure to higher levels of free Resveratrol and its metabolites.

Example 3. Oligonol-SR Formula

Oligonol (79.7% polyphenols) was formulated using a combination of HPMC, Carnauba wax and b-cyclodextrin. The formulation Oligonol-SR, is a granular free flowing powder containing 50% Oligonol, suitable for hard gelatin capsules and tablets.

Oligonol-SR Dissolution Test

The objective of this study was to determine the in vitro dissolution profile and sustained release properties of the Oligonol-SR formulation in comparison with Oligonol powder. The studies were done using a bio-relevant media, which can predict the bioavailability in vivo.

Samples Tested

Oligonol powder (79.7% polyphenols)
Oligonol-SR (50% polyphenols)

Dissolution Test

The in vitro dissolution study was performed using the Varian 7020 dissolution tester with the basket configuration at 37° C., 100 rpm. The samples equivalent to 25 mg Oligonol filled in hard gelatin capsules were used for the study. The capsules were introduced into 750 ml of 0.1N HCl (simulated gastric fluid without enzymes, SGF) maintained at 37° C. At the end of 1 and 2 hrs, 2 ml of the sample was withdrawn and filtered through 10μ-syringe filter. The removed volume was replaced each time with fresh medium. Total polyphenols were determined by Folin-Ciocalteu method using Gallic acid (Sigma) as standard.

At the end of 2 hr, the pH of the medium was adjusted to 6.5 (Simulated intestinal fluid without enzymes, SIF) with an appropriate amount of 0.2M tribasic sodium phosphate solution equilibrated to 37° C. Polysorbate 80 at 0.25% (simulating fed state) dissolved in water was added to the medium. Aliquots were withdrawn at 4,6,9 and 12 hrs for analysis as described before and the removed volume was replaced with fresh medium each time.

Observations

FIG. 6 presents the dissolution profile of Oligonol powder and Oligonol-SR. With the Oligonol powder, nearly 95% of the dose was in solution by 4 hours. The Oligonol-SR formula showed sustained release over a period of 12 hrs, with 95% of the dose released at 12 hrs.

Oligonol-SR Bioavailability: A Pilot Study

The objective of this human study was to determine the uptake of Oligonol-SR powder in comparison with Oligonol powder.

Clinical Study Protocol

Oligonol-SR formulation and Oligonol powder equivalent to 200 mg Oligonol were used for the study. The samples were provided in hard gelatin capsules. The crossover study was done using two healthy subjects who were not consuming Oligonol supplements. The subjects were asked not to consume high polyphenol containing foods or beverages (coffee, tea, or wine) for 48 hours before the study. On the day of the study, 5 ml of blood was collected in EDTA tubes to permit establishment of baseline value. Oligonol-SR capsules were administered after a low polyphenol containing breakfast with no dairy products. Blood samples were drawn as before at 1, 2, 4, 6, and 8 hrs post-dose. Only water was provided during the period of study. The blood samples were stored on ice protected from light and the plasma was separated by centrifugation within 1 hr of collection and stored at –70° C. until analysis. After a 7-day washout period the protocol was repeated for the control Oligonol powder capsules.

Oligonol Analysis

Plasma Oligonol was determined by the Prussian Blue method (Evaluation of safety and toxicity of oligomerized polyphenol Oligonol, Fujii, H., Sun, B., Nishioka H., Hirose, A. and Aruoma, O. I., *Food and Chemical Toxicology*, 2007, 45: 378-387). For deproteinization, 0.24 ml of the plasma was mixed with 0.08 ml of 60% perchloric acid, and 1.2 ml of n-butanol. The mixture was vortex mixed for 10 sec and centrifuged at 4° C., 10,000 rpm for 10 min. 0.4 ml of the supernatant was evaporated under nitrogen. To the residue 2 ml of ferric chloride solution (0.1M in 0.1N HCl) was added and the reaction was initiated by adding 0.16 ml of 0.01M Potassium ferricyanide solution. The absorbance was determined at 720 nm exactly after 20 min at room temperature. The plasma polyphenol content (microgram/ml plasma) was quantified by using Gallic acid (Sigma) as the standard.

Results

FIG. 7 presents the plasma total Oligonol profile from Oligonol-SR and Oligonol powder. Oligonol powder showed a rapid absorption with a peak at $T_{max}$ of 2 hrs post-dose. After 2 hrs, the plasma levels of total Oligonol declined rapidly with a small increase at 6 hrs and by 8 hrs, the levels were close to baseline. Oligonol-SR also showed a $T_{max}$ at 2 hr, but a higher $C_{max}$ (maximum concentration at $T_{max}$) and a second prominent absorption peak at 6 hrs post dose and a higher plasma level at 8 hrs post dose.

The average area under the curve ($AUC_{0-8hr\ mcg/(ml*hr)}$) for plasma Oligonol was 6.6 (Oligonol-SR) and 2.76 (Oligonol powder). The ratio of Oligonl-SR to Oligonol powder AUC was 2.39.

Observations

Oligonol powder is absorbed rapidly and eliminated by ~8 h post dose. The results of the study indicate that Oligonol-SR formulation extends the systemic exposure to higher levels of Oligonol.

Example 4. PQQ-SR Formula

PQQ (99%) was formulated using a combination of HPMC, Carnauba wax and b-cyclodextrin. The formulation PQQ-SR, is a granular free flowing powder containing 50% PQQ, suitable for hard gelatin capsules and tablets.

PQQ-SR Dissolution Test

The objective of this study was to determine the in vitro dissolution profile and sustained release properties of the PQQ-SR formulation in comparison with PQQ powder. The studies were done using a bio-relevant media, which can predict the bioavailability in vivo.

Samples Tested

PQQ powder (99%)
PQQ-SR (50% PQQ)

Dissolution Test

The in vitro dissolution study was performed using the Varian 7020 dissolution tester with the basket configuration at 37° C., 100 rpm. The samples equivalent to 20 mg PQQ filled in hard gelatin capsules were used for the study. The capsules were introduced into 750 ml of 0.1N HCl (simulated gastric fluid without enzymes, SGF) maintained at 37° C. At the end of 1 and 2 hrs, 2 ml of the sample was withdrawn and filtered through 10μ-syringe filter. The removed volume was replaced each time with fresh medium. PQQ was determined by spectrophotometry at 330 nm.

At the end of 2 hr, the pH of the medium was adjusted to 6.5 (Simulated intestinal fluid without enzymes, SIF) with an appropriate amount of 0.2M tribasic sodium phosphate solution equilibrated to 37° C., Polysorbate 80 at 0.25% (simulating fed state) dissolved in water was added to the medium. Aliquots were withdrawn at 4, 6, 9, and 12 hrs for analysis as described before and the removed volume was replaced with fresh medium each time.

Observations

The dissolution profile (FIG. 8) shows a sustained release of PQQ from the PQQ-SR formulation. By 12 hrs, ~95% of the dose was in solution in a micronized form, less than 10μ particle size. With the control PQQ powder, 100% of the dose was in solution by 4 hrs. The results indicate that the PQQ-SR formulation may increase the residence time of PQQ and enhance the beneficial effects in vivo.

PQQ-SR Bioavailability: A Pilot Study

The objective of this human study was to determine the uptake of PQQ from PQQ-SR powder in comparison with 99% PQQ powder.

Clinical Study Protocol

PQQ-SR formulation and PQQ powder equivalent to 40 mg PQQ were used for the study. The samples were provided in hard gelatin capsules. The crossover study was done using two healthy subjects. On the day of the study, 7 ml of blood was collected in EDTA tubes to permit establishment of baseline value. PQQ-SR capsules were administered after breakfast and blood samples were drawn as before at 1, 2, 4, 7, and 9 hrs post-dose. The samples were stored on ice protected from light and the plasma was separated by centrifugation within 1 hr of collection and stored at −70° C. until analysis. After a 7-day washout period the protocol was repeated for the control PQQ powder capsules.

PQQ Extraction and Analysis

Plasma PQQ was extracted using n-butanol and HCl followed by SepPak C-18 clean up of the extract as described by Suzuki et al. (Extractions of pyrroloquinoline quinone from crude biological samples, Suzuki, O., et al., *Life Sci.,* 47: 2135-41, 1990). PQQ was estimated by using the enzymatic method as described by Geiger and Gorisch (Enzymatic determination of pyrroloquinoline quinone using crude membranes from *E. coli,* Geiger, O. and Gorisch, H., *Anal Biochem.,* 164: 418-23, 1987). The method measures only the free PQQ in the plasma.

Results and Observations

FIG. 9 presents the uptake of PQQ from PQQ-SR and 99% PQQ powder. PQQ-SR showed a $T_{max}$ of 2 hr with a higher plasma PQQ level compared to PQQ powder followed by sustained release until 9 hrs. The plasma levels remained high at 9 hrs, indicating sustained release for >9 hrs. The control PQQ powder showed a $T_{max}$ at 2 hrs and the plasma level reached near baseline by 9 hours. The average area under the curve ($AUC_{0-9hr\ ng/(ml*hr)}$) for PQQ-SR was 69.66 and for the control PQQ 31.41. The ratio of PQQ-SR to control PQQ AUC was 2.2.

While the compositions and methods have been described with reference to various embodiments, those skilled in the art will understand that various changes may be made and equivalents may be substituted for elements thereof without departing from the scope and essence of the disclosure. In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

We claim:

1. A nutraceutical composition comprising:
    a nutraceutical present in an amount of from about 1% to about 60% by weight, wherein the nutraceutical is selected from the group consisting of a carotenoid, a carotenoid ester, a curcuminoid, policosanol, silymarin, baicalein, quercetin, a plant sterol, a vitamin, alpha lipoic acid, a sesquiterpene lactone, and mixtures thereof;
    a lipid present in an amount of from about 0.5% to about 20% by weight;
    a surfactant present in an amount of from about 10% to about 30% by weight, wherein the surfactant is selected from the group consisting of a non-ionic polysorbate, a polyglycerol ester of a fatty acid, and mixtures thereof;
    a polymer present in an amount of from about 1% to about 50% by weight;
    an excipient present in an amount of from about 1% to about 50% by weight, wherein the excipient is selected from the group consisting of microcrystalline cellulose, silica, maltodextrin, potato starch, rice flour, and mixtures thereof;
    wherein the composition is a micronized, water-dispersible powder, wherein the powder comprises a plurality of particles, each of the plurality of particles comprising the nutraceutical and comprising a particle size of from about 1 μm to about 10 μm.

2. The composition of claim 1, wherein the polymer is selected from the group consisting of carboxymethyl cellulose, ethyl cellulose, hydroxypropyl methylcellulose, alginic acid sodium salt, a dextrin, carrageenan, a cyclodextrin, and mixtures thereof.

3. The composition of claim 1, wherein the composition comprises an amount of from about 1 wt. % to about 60 wt. % of the nutraceutical, an amount of from about 1 wt. % to about 7 wt. % of the lipid, an amount of from about 10 wt. % to about 30 wt. % of the surfactant, and an amount of from about 10 wt. % to about 20 wt. % of the polymer.

4. The composition of claim 3, wherein the curcuminoid is curcumin and is present in an amount of about 25 wt. %.

5. The composition of claim 4, wherein the lipid is isopropyl myristate, the surfactant is polysorbate 80, and the polymer is a mixture of hydroxypropyl methylcellulose and sodium alginate.

6. A nutraceutical composition comprising:
    a nutraceutical present in an amount of from about 1% to about 60% by weight, wherein the nutraceutical is selected from the group consisting of phenolic compounds, bioactive polysaccharides, amino acids, and mixtures thereof;

a polymer present in an amount of from about 1% to about 50% by weight;

a cyclodextrin present in an amount of from about 1% to about 30% by weight; and a lipid present in an amount of from about 0.5% to about 20% by weight;

wherein the composition is a micronized, water-dispersible powder, wherein the powder comprises a plurality of particles, each of the plurality of particles comprising the nutraceutical and comprising a particle size of from about 1 μm to about 10 μm.

7. The composition of claim 6, wherein the polymer is selected from the group consisting of cellulose, ethyl cellulose, hydroxypropyl methylcellulose, alginic acid sodium salt, a dextrin, carrageenan, and mixtures thereof.

8. The composition of claim 7, wherein the lipid is a solid at room temperature and is selected from the group consisting of a saturated fat, a food grade wax, a shellac, and mixtures thereof.

9. The composition of claim 8, wherein the cyclodextrin is selected from the group consisting of α-cyclodextrin, β-cyclodextrin, γ-cyclodextrin, and mixture thereof.

10. The composition of claim 9, wherein the composition comprises an amount of from about 1 wt. % to about 60 wt. % of the nutraceutical, an amount of from about 5 wt. % to about 15 wt. % of the lipid, and an amount of from about 10 wt. % to about 20 wt. % of the polymer.

11. The composition of claim 9, wherein the nutraceutical is resveratrol.

12. The composition of claim 9, wherein the nutraceutical is a mixture of polyphenols, wherein the polyphenols are proanthocyanidins.

13. The composition of claim 9, wherein the nutraceutical is selected from the group consisting of catechin, rutin, and pyrroloquinoline quinone.

14. The composition of claim 11, wherein the composition comprises about 30 wt. % of the nutraceutical.

15. The composition of claim 12, wherein the composition comprises about 30 wt. % of the nutraceutical.

16. The composition of claim 12, wherein the composition comprises about 50 wt. % of the nutraceutical.

17. The composition of claim 1, wherein the silica consists of a bamboo silica.

18. The composition of claim 1, wherein the composition increases an oral bioavailability of the nutraceutical in comparison with an oral bioavailability of a 95% pure powder of the nutraceutical.

19. The composition of claim 6, wherein the composition increases an oral bioavailability of the nutraceutical in comparison with an oral bioavailability of a 95% pure powder of the nutraceutical.

* * * * *